United States Patent [19]
Saven et al.

[11] Patent Number: 5,510,336
[45] Date of Patent: Apr. 23, 1996

[54] 2-HALO-2'-DEOXYADENOSINE TREATMENT FOR HISTIOCYTOSIS

[76] Inventors: Alan Saven, 13016 Walking Path Pl., San Diego, Calif. 92130; Lawrence D. Piro, 1339 Dell Crest La., La Jolla, Calif. 92037

[21] Appl. No.: 301,243

[22] Filed: Sep. 6, 1994

[51] Int. Cl.⁶ ........................................ A61K 31/70
[52] U.S. Cl. ............................ 514/46; 536/27.63
[58] Field of Search ............................ 514/46; 536/27.63

[56] References Cited

U.S. PATENT DOCUMENTS

| | | | |
|---|---|---|---|
| 5,106,837 | 4/1992 | Carson et al. | 514/46 |
| 5,310,732 | 5/1994 | Carson et al. | 514/46 |
| 5,401,724 | 3/1995 | Beutler | 514/46 |
| 5,424,296 | 6/1995 | Saven et al. | 514/46 |

OTHER PUBLICATIONS

Favara (II), "Langerhans' Cell Histiocytosis Pathobiology and Pathogenesis," *Seminars in Oncology*, 18(1), 3–7 (1991).
Komp et al, "Introduction: The Histiocytic Syndromes," *Seminars in Oncology*, 18(1), 1–2 (1991).
Willman et al, "Langerhans'–Cell Histiocytosis (Histiocytosis X)–A Clonal Proliferative Disease," *The New England J. of Medicine*, 331(3), 154–160 (1994).
Komp, "Langerhans' Cell Histiocytosis," *The New England J. of Medicine*, 316(12), 747–748 (1987).
Gotoh et al., "Induction of Unresponsiveness to Islet Allograft by Anti–LFA–1 Monoclonal Antibody Treatment," *Transplantation Proceedings*, 25(1, Book II), 973–974 (1993).
Chapal et al., "Effects of Adenosine, Adenosine Triphosphate and Structural Analogs on Glucagon Secretion from the Perfused Pancreas of Rat In Vitro," *British J. Pharmacology*, 83, 927–933 (1984).
Berkow et al. (eds.), *Merck Manual of Diagnosis and Therapy, Sixteenth Ed.*, Merck Research Labs., Rahway, NJ, 1992, see pp. 720, 1354–1355 & 2206–2211.
Saven et al. (II), "2–Chlorodeoxyadenosine to Treat Refractory Histiocytosis X," *N. Engl. J. Med.*, 329(10), 734–735 (1993).
Saven et al. (III), "2–Chlorodeoxyadenosine–induced Complete Remission in Langerhans–Cell Histiocytosis," *Annals Internal Medicine*, 121(6), 430–432 (1994).
Saven, et al., *The New Engl. Jrnl. of Med.*, pp. 734–735, Sep. 2, 1993.
Histiocytosis Syndromes Classification, Diagnostic Features and Current Concepts Blaise E. Favara, *Leukemia and Lymphoma*, 2:141–150, Sep. 14, 1989.
Histiocytosis Saven, et al., *Annals of Internal Medicine*, No. 6, 121:3 pgs., Sep. 15, 1994.

*Primary Examiner*—Douglas W. Robinson
*Assistant Examiner*—L. Eric Crane
*Attorney, Agent, or Firm*—Fish & Richardson

[57] ABSTRACT

An improved method for treating Class I histiocytosis, Langerhans cell histiocytosis, is disclosed. In accordance with that method, a therapeutically effective amount of a 2-halo-2'-deoxyadenosine is administered to a host mammal such as a human patient having histiocytosis in an amount of about 0.5 to 0.9 mg/kg of body weight over a course of about 5 to 9 days for up to two courses.

12 Claims, No Drawings

2-HALO-2'-DEOXYADENOSINE TREATMENT FOR HISTIOCYTOSIS

BACKGROUND OF THE INVENTION

1. Field of the Invention

This invention relates to the treatment of histiocytosis, and more particularly to a method for treating histiocytosis that utilizes a 2-halo-2'-deoxyadenosine.

2. Description of Related Art Histiocytes and lymphocytes, the key constituents in lesions of the histiocytosis syndromes, show an enormous capacity for metamorphosis, functional change, secretion of cytokines, and interaction with one another and other cells, especially endothelial cells. For instance, histiocytes and lymphocytes may be either "down" or "up" regulated by certain "activators" causing them to secrete some cytokines, to stop secreting other cytokines, to proliferate, phagocytize, transform, etc.—a complex paradigm referred to as "activation."

Histiocytes are bone marrow derived cells of the mononuclear phagocytic system (MPS) and dendritic cells that are possibly a subset of the MPS. Histiocytes are known to be extremely dynamic and their morphologic and immunologic traits are capricious; to a large degree that capriciousness is influenced by their interaction with other cells, particularly lymphocytes, and by biological response modifiers or cytokines.

Normal Langerhans cells and Langerhans cell histiocytosis (LCH) cells are dendritic cells that have cytological, functional and ultrastructural characteristics shared by other histiocytes, but they are unique in that they contain Langerhans cell granules (M. S. Birbeck et al, *J. Invest. Dermatol.* 37:51–64, 1961). It is believed by some that LCH cells are not derived from normal Langerhans cells at all, but they could stem from circulating dendritic cells or even ordinary histiocytes that have, under pathological conditions, acquired characteristic markers of Langerhans cells (B. E. Favara et al, *Hematol./Oncol. Clin. No. Amer.*, 1:75–96, 1987; J. S. Greenberger et al, *Medicine*, 1:311,338, 1981; M. E. Osband et al., *New Eng. J. Med.*, 304:146–153, 1981). Others believe that Langerhans-cell histiocytosis results from the proliferation and accumulation of tissue histiocytes. There is not a great depth of knowledge in the art about the origin of some histiocytes (Favara et al., *Leukemia and Lymphoma*, 2:141–150, 1990).

Histiocytosis is clinically manifested as osteolytic lesions, hypothalamic insufficiency, and seborrheic and vesiculopustular lesions on the scalp, perineum, rectum, and vulva (J. E. Groopman et al, *Ann Intern Meal.* 94.:95–107, 1981). Heretofore, treatment has been largely palliative and includes corticosteroids, alkylating agents, antimetabolites, vinca alkaloids, and irradiation (D. M. Komp, *Semin Oncol.* 18:18–23, 1991 ). Combination chemotherapy offers no advantage over the use of single agents and is associated with greater toxicity. 2-Chlorodeoxyadenosine (2-CdA) (cladribine, Leustatin [Ortho Biotech, Raritan, N.J.]), a purine analog with activity in indolent lymphoproliferative disorders and myeloid leukemias (A. Saven et al, *N. Engl. J. Med.* 330:691–697, 1994; A. Saven et al., *Ann. Intern. Med.*, 120:784–91, 1994) is potently toxic to monocytes in vitro.

2-Halo-2'-deoxyadenosines have been reported to be useful in treating non-tumor diseases categorized as monocyte mediated diseases. For instance, PCT patent application number PCT US89/01088, published on 9/21/89, discloses that diseases resulting from chronically infected monocytes and inflammatory diseases resulting from autoimmune disorders caused by monocytes, such as rheumatoid arthritis, can be treated with 2-CdA, which exhibits potent cytotoxicity toward monocytes. U.S. Pat. No. 5, 106,837, issued Apr. 21, 1992 discloses additional monocyte mediated diseases that respond to treatment with 2-CdA: hemolytic anemia, Chagas disease, Leishmaniasis, toxoplasmosis, malaria, pneumocystis sarcoidosis, chronic granulomatous hepatitis, Wegener's granulomatosis, Paget's disease, atherosclerosis, inflammatory bowel disease, and granulomatous uveitis. Treatment of multiple sclerosis with 2CdA is additionally disclosed in U.S. Pat. No. 5,310,732 published Sept. 2, 1993.

In those disclosures, the 2-halo-2'-deoxyadenosine was described as acting primarily against monocytes. The 2-halo-2'-deoxyadenosine used in those studies was 2-chloro-2'-deoxyadenosine (2-CdA), which was used at a dosage of 0.1 mg/kg body weight/day administered by infusion over a five-day time period with courses at about monthly intervals for a total of three courses of treatment. Patient monocyte levels dropped substantially to zero during treatment cycles and rose to about pretreatment levels about ten days after 2-CdA infusion was stopped. Patients showed improvement in various assays for rheumatoid arthritis during the treatment. Follow-up letters from personal physicians to one of those inventors, Dr. Carson, indicated a white cell count at about 50 percent of pretreatment values that lasted for one to three years after treatment ceased. Those personal physicians also reported greater patient improvements that became evident several months after cessation of treatment.

The teachings of the art contain a single reference to treatment of histiocytosis with a 2-chlorodeoxyadenosine. Saven et al., *New England Journal of Medicine*, 329:734–735, 1993, reported that 2-CdA when administered to a patient with symptoms histologically consistent with a diagnosis of Langerhans-cell histiocytosis, sometimes referred to as histiocytosis X (a Class I histiocytosis) was successfully treated with 2-Cda. A 33 year old woman, who had been treated with high-dose steroid therapy and vinblastine, oral etoposide, vincristine, cyclophosphamide, and methotrexate over a two year period, was administered four courses of 2-Cda at 0.1 mg per kilogram of body weight per day for 7 days by continuous intravenous infusion at intervals of 28 to 35 days, except that the second course was delayed by development of dermatomal herpes zoster and later complicated by transient grade 3 neutropenia. The patient had experienced complete remission for more than 17 months at the time of the report.

The toxicity of CdA to monocytes and lymphocytes has also been reported by Carrera et al., *J. Clin. Invest.*, 86:1480–1488 (1990). That paper also disclosed the use of CdA in clinical trials in patients having chronic lymphoid malignancies. Toxicity in vitro of CdA and 2-fluorodeoxyadenosine (FdA) toward resting and proliferating lymphocytes had been reported by the same research group in Carson et al., *Proc. Natl. Acad. Sci., USA*, 79:3848–3852 (1982). Priebe et al., *Cancer Res.*, 48:4799–4800 (1988) reported that CdA elevated in vivo NK cell activity at concentrations (6–25 mg/kg/day) that inhibited T-dependent and T-independent antibody responses in mice.

Carson et al., *Blood*, 62(4):737–743 (1983) reported on the in vitro effects of CdA on a variety of cells and cell lines including resting normal T lymphocytes, slowly dividing malignant T cells from a patient with mycosis fungoides and CCRF-CEM malignant T lymphoblasts. A time- and concentration-dependent relation for CdA cytotoxicity was reported, with the malignant T lymphoblasts being more sensitive to CdA than were resting normal T lymphocytes.

Carson et al., *Proc. Natl. Acad. Sci, USA,* 81:2232–2236 (1984) and Piro et al., *Blood,* 72:1069–1073 (1988) also reported on the positive effect of CdA on various human lymphocytic neoplastic disorders, including chronic lymphocytic leukemia (CLL), and had previously reported that CdA was an effective agent for treating the murine B cell L1210 lymphoid leukemia in vivo. Carson et al., *Blood,* 62:737–743 (1983).

The Piro et al., *Blood,* 72:1069–1073 (1988) studies with CLL illustrated some partial responses (4/18) and other clinical improvements (6/18), but no complete responses. Those workers also reported that in vitro studies of the sensitivity of patient CLL cells to CdA did not correlate with in vivo findings. Other in vitro studies indicated that T cells were more vulnerable than B cells to CdA, but that difference was not clinically apparent. Saven et al., *N. Engl. J. Med.,* 330(10):691–697 (1994).

Avery et al., *Cancer Res.,* 49:4972–4978 (1989) also reported the effects of CdA on T-lymphoblastic, B-lymphoblastic and non-T, non-B cell lines, as well as in vivo effects on mice inoculated with L1210 leukemia of 2-bromo-2'-deoxyadenosine (BrdA) at 11.25 mg/kg/injection alone and paired with other therapeutic agents. Saven and Piro, *N. Engl. J. Med.,* 330(10):691–697 (1994) reported on the use of CdA and 2'-deoxycofurmycin in treating hairy cell leukemia, a B cell neoplasm.

Parsons et al., *Biochem. Pharmacol,* 35:660–665 (1986) reported results with two human melanoma cell lines that were sensitive to each of CdA, FdA and BrdA. Saven et al., *J. Clin. Oncol.,* 11(4):671–678 (1993) noted that because of the interferon-sensitivity of hairy cells and the sensitivity of those cells to CdA, melanoma and renal cell carcinoma that are also sensitive to interferon might be similarly sensitive to CdA in vivo, as were the two melanoma cell lines reported by Parsons et al. sensitive in vitro. The results of the above Saven et al. CdA studies with human patients with melanoma (nine patients) and renal cell carcinomas (two patients) showed no responses to the treatment. Contrarily, two of seven patients with astrocytomas, a tumor not noted to be sensitive to interferon, showed marked improvement. Thus, the attempted parallel between tumor cell interferon-sensitivity and successful treatment with CdA was not evident from those studies. In addition, the in vitro sensitivity of the assayed melanoma cell lines to CdA was not observed in vivo, in a clinical setting.

Reiter et al., *Purine and Pyrimidine Metabolism in Man VII,* Part A, Harness et al., eds., Academic Press, New York (1991) pages 69–73 reported on the combined use of interferon-α (IFN-α) and CdA upon various tumor cell lines including a hairy cell leukemia-like cell line, (Eskol 17), a cervical carcinoma cell line, a chronic myelogenous leukemia cell line and an AIDS-related Kaposi's sarcoma. They reported an additive time- and dose-dependent effect on cell growth, but no synergy between the two treating agents. Those workers also reported that CdA did not affect NK cell-mediated cytotoxicity of Eskol 17 cells in the presence or absence of IFN-α. Although CdA neither affected the activity of NK cells nor was involved in the priming of NK cells by IFN-α, CdA was reported to affect the target tumor cells.

Beutler et al., *Leukemia and Lymphoma,* 5:1–8 (1991) reported that CdA treatment provided mixed results in patients with T cell lymphomas that were resistant to conventional therapies. Here, of the evaluable patients, some had complete remissions (3/17), some had partial remissions (5/17) and more than half had no response (9/17). This paper also reported results with low grade as well as high and intermediate grades of non-Hodgkin's lymphomas. For the low grade disease, just under 40 percent of the evaluable patients (15/40) exhibited a complete or partial response, and the remainder exhibited no response (25/40). Somewhat poorer results were found for patients with intermediate or high grade diseases; 7/26 complete or partial response and 9/26 no response. Results with other hematologic disorders involving fewer patients were also reported.

Petzer et al., *Blood,* 78(10):2583–2587 (1991) reported the effects CdA on various progenitor cells from bone marrow, including so-called T lymphocyte colony forming cells (CFU-TL). Those authors reported a dose-dependent inhibition of the growth of CFU-TL in vitro, and also reported that the drug concentration needed for complete inhibition much higher than that required for erythroid and granulocyte/macrophage progenitors. Those authors commented that the more mature the treated colony forming cells were, the higher the CdA concentration that was needed to inhibit proliferation. They also noted that the assay they used probably does not detect the true T lymphocyte progenitor, and that their assay may not accurately reflect regulatory mechanisms in vivo.

It is thus seen that the effects of a 2-halo-2'-deoxyadenine upon tumor growth are not yet predictable as to which tumors are sensitive, although once activity for one compound is found, the other 2-halo-dA's also possess that activity; that in vitro studies may not correlate with in vivo, patient studies; and that the effects of a drug from this group such as CdA upon a tumor cell type can vary widely from patient to patient even where a positive inhibition of growth is found.

Other studies, Montgomery et al., *J. Am. Chem. Soc.,* 82:463–468 (1959), indicated that 2-fluoroadenosine exhibits a relatively high degree of cytotoxicity. Those workers reported that C57 black mice implanted with Adenocarcinoma 755 (Ad755) could tolerate only about 1 milligram per kilogram of body weight. 2-Fluoroadenosine was found to be inactive at that level against Ad755 as well as leukemia L1210 and the Erlich ascites tumor.

Hence, the need exists for new and improved methods of treating histiocytosis utilizing in vivo administration of a 2-halo-2'-deoxyadenosine as the active agent.

SUMMARY OF THE INVENTION

The present invention contemplates a method for treating histiocytosis in a mammalian host such as a human. The compound utilized in the present method as active agent in that treatment is a 2-halo-2'-deoxyadenosine, which has a structure that corresponds to that of Formula I:

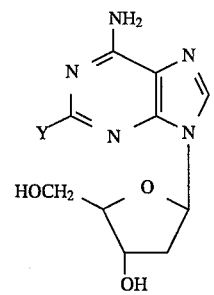

wherein Y is a halogen that is fluoro, chloro or bromo, preferably chloro.

One embodiment of the methods of this invention contemplates administering to a mammalian host having the clinical symptoms of histiocytosis a composition comprising a pharmacologically acceptable carrier that contains dissolved or dispersed therein a therapeutically effective dose of a substituted adenine derivative having a structure that corresponds to that of Formula I or a pharmacologically acceptable acid addition salt thereof as an active ingredient or agent. Exemplary therapeutic dosages range from about 0.5 to 0.9 mg/kg of body weight administered, preferably by infusion, over a course of from about 5 to 9 days, with the preferred course of administration being from about 0.05 to about 0.15 mg/kg/day, most preferably about 0.1 mg/kg/day for 5 to 7 days. Typically the dosage is administered by infusion at about monthly intervals for no more than a total of two courses of treatment. It is most preferred that a single course of treatment be employed in treatment of Langerhans cell histiocytosis.

The substituted adenine derivative of Formula II, below, 2-chloro-2'-deoxyadenosine (2-CdA); i.e., where Y is chloro, is a particularly preferred adenine derivative of Formula I.

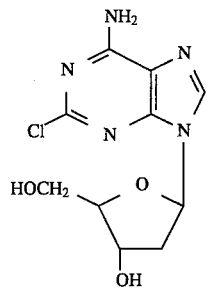

The present invention has several benefits and advantages. Unexpectedly, the improved methods of this invention can provide alleviation from the symptoms of histiocytosis, such as Langerhans cell histiocytosis, using a greatly reduced amount of drug to avoid toxic side effects to T-cells, B-cells and other lymphocytes. The mechanism of response to CdA in Langerhans cell histiocytosis has not been elucidated and does not form a part of this invention, but it is believed that it may involve direct cytotoxicity to monocytes or the putative Langerhans cell, or may be mediated through its T-cell immunosuppressive effects (C. J. Carrera et al., *Blood.* 76 (Suppl 1):260a, 1990).

A particular advantage of the present invention is that use of its method can substantially reduce a patient's dependence on prednisone or other drugs whose prolonged use can itself be detrimental to the patient.

Still another advantage of the invention is that use of its methods can rapidly improve the pathological condition of the diseases tissue so that objective indicia of disease are greatly reduced.

Still further benefits and advantages of the invention will be apparent to those skilled in the art from the description that follows.

DETAILED DESCRIPTION OF THE INVENTION

The present invention contemplates a method for treating histiocytosis. A contemplated method utilizes a 2-halo-2'-deoxyadenosine (an adenine derivative) as an active agent compound in a composition that is administered to a mammalian host in need of such a treatment; i.e., having histiocytosis.

A. Compounds

A compound utilized in the present invention is a 2-halo-substituted-2'-deoxyadenosine derivative whose structure is represented by Formula I:

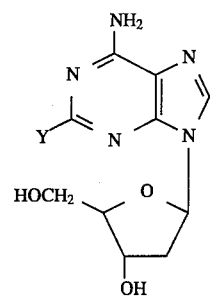

wherein Y is a halogen that is fluoro, chloro or bromo. Y is preferably chloro in which case the compound has a structure represented by Formula II, below, and can be named 2-chloro-9,1'-beta-2'-deoxy-D-ribofuranosyladenine, more simply as 2-chloro-2'-deoxyadenosine or most simply as 2-CdA.

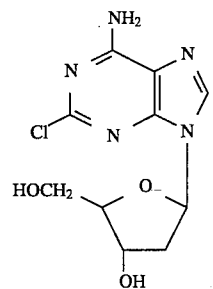

In the above formulas, and in all other formulas shown herein, hydrogen atoms on the purine and furanosidyl rings that are not needed to show conformation about a particular bond are not shown. Thus, for example, the 7-position adenine hydrogen is not shown.

It is also to be understood that the D isomers of compounds of the formulas are the isomers contemplated. It is further to be noted that the designation "halo" used herein is meant to include fluorine, chlorine and bromine derivatives, and to exclude iodine derivatives, which are unstable and decompose, and astatine derivatives that are radioactive. Where specific halogen derivatives are intended, those compounds are named specifically.

The pharmacologically acceptable salts of a compound of Formula I or Formula II are also utilized. The phrase "pharmacologically acceptable salts," as used herein, refers to non-toxic acid addition salts that are generally prepared by reacting a compound with a suitable organic or inorganic acid. Representative salts include the hydrochloride, hydrobromide, sulfate, phosphate, citrate, acetate, maleate and the like.

B. Compositions A compound of Formula I and its pharmacologically acceptable salts dissolved or dispersed in or together with a pharmacologically acceptable carrier constitutes a composition useful in a method of this invention. A compound of Formula II and its pharmacologically acceptable salts is preferred for use in both short and long term treatment. Although a compound of Formula land its pharmacologically acceptable salts can be administered as the pure chemical, it is preferred that it be administered as a pharmaceutical composition. In either event, a contemplated compound is administered in an amount sufficient to provide a therapeutically effective dose as is discussed hereinafter.

Accordingly, the present invention utilizes a pharmaceutical composition comprising a therapeutically effective dose of a compound of Formula I or Formula II, or a pharmacologically acceptable salt thereof, hereinafter referred to as the "active ingredient" or "agent," dissolved or dispersed in a pharmacologically acceptable carrier or diluent.

A pharmaceutical composition is prepared by any of the methods well known in the art of pharmacy, all of which involve bringing into association the active compound and the carrier therefor. For therapeutic use, a compound utilized in the present invention can be administered in the form of conventional pharmaceutical compositions. Such compositions can be formulated so as to be suitable for oral or parenteral administration, or as suppositories. In these compositions, the agent is typically dissolved or dispersed in a physiologically tolerable carrier or diluent.

A carrier or diluent is a material useful for administering the active compound and must be "pharmacologically acceptable" in the sense of being compatible with the other ingredients of the composition and not deleterious to the recipient thereof. Thus, as used herein, the phrases "physiologically tolerable" and "pharmacologically acceptable" are used interchangeably and refer to molecular entities and compositions that do not produce an allergic or similar untoward reaction, such as gastric upset, dizziness and the like, when administered to a mammal, particularly, a human. The pharmacologically tolerable carrier can take a wide variety of forms depending upon the preparation desired for administration and the intended route of administration.

As an example of a useful composition, a compound of Formula 1 can be utilized in liquid compositions such as sterile suspensions or solutions, or as isotonic preparations containing suitable preservatives. Particularly well-suited for the present purposes are injectable media constituted by aqueous injectable isotonic and sterile saline or glucose solutions. Additional liquid forms in which these compounds can be incorporated for oral administration include flavored emulsions with edible oils such as cottonseed oil, sesame oil, coconut oil, peanut oil, and the like, as well as elixirs and similar pharmaceutical vehicles.

An active agent can also be administered in the form of liposomes. As is known in the art, liposomes are generally derived from phospholipids or other lipid substances. Liposomes are formed by mono- or multilamellar hydrated liquid crystals that are dispersed in an aqueous medium. Any non-toxic, lo physiologically acceptable and metabolizable lipid capable of forming liposomes can be used. The present compositions in liposome form can contain stabilizers, preservatives, excipients, and the like in addition to the agent. The preferred lipids are the phospholipids and the phosphatidyl cholines (lecithins), both natural and synthetic.

Methods to form liposomes are known in the art. See, for example, Prescott, Ed., *Methods in Cell Biology*, Volume XIV, Academic Press, New York, N.Y. (1976), p. 33 et seq.

An agent of Formula I can also be used in compositions such as tablets or pills, preferably containing a unit dose of the compound. To this end, the agent (active ingredient) is mixed with conventional tableting ingredients such as corn starch, lactose, sucrose, sorbitol, talc, stearic acid, magnesium stearate, dicalcium phosphate, gums, or similar materials as non-toxic, physiologically tolerable carriers. The tablets or pills can be laminated or otherwise compounded to provide unit dosage forms affording prolonged or delayed action.

It Should be understood that in addition to the aforementioned carrier ingredients the pharmaceutical formulation described herein can include, as appropriate, one or more additional carrier ingredients such as buffers, flavoring agents, binders, surface active agents, thickeners, lubricants, preservatives (including antioxidants) and the like, and substances included for the purpose of rendering the formulation isotonic with the blood of the intended recipient.

The tablets or pills can also be provided with an enteric layer in the form of an envelope that serves to resist disintegration in the stomach and permits the active ingredient to pass intact into the duodenum or to be delayed in release. A variety of materials can be used for such enteric layers or coatings, including polymeric acids or mixtures of such acids with such materials as shellac, shellac and cetyl alcohol, cellulose acetate phthalate, and the like. A particularly suitable enteric coating comprises a styrene-maleic acid copolymer together with known materials that contribute to the enteric properties of the coating. Methods for producing enteric coated tablets are described in U.S. Pat. No. 4,079,125 to Sipos, which is herein incorporated by reference.

The term "unit dose", as used herein, refers to physically discrete units suitable as unitary dosages for administration to warm blooded animals, each such unit containing a predetermined quantity of the agent calculated to produce the desired therapeutic effect in association with the pharmaceutically acceptable diluent. Examples of suitable unit dosage forms in accord with this invention are tablets, capsules, pills, powder packets, granules, wafers, cachets, teaspoonfuls, dropperfuls, ampules, vials, segregated multiples of any of the foregoing, and the like.

C. Methods

As noted earlier, a method of treating histiocytosis is contemplated here. There are three classes of histiocytosis, Classes I–III as follows:

Class I is directed to Langerhans cell histiocytosis, of which eosinophilic granuloma, Hand-Schuller-Christian disease, Letterer-Siwe disease are different presentations of this condition. Class I histiocytosis is also termed histiocytosis X or reticuloendothelial granulomatosis.

Class II is directed to hemophagocytic syndromes, e.g. familial hemophagocytic lymphohistiocytosis, infection associated hemophagocytic syndrome, sinus histiocytosis with massive lymphadenopathy are different presentations of Class II histiocytosis.

Class III is directed to malignant histiocytosis syndromes, e.g., leukemia, malignant histiocytosis (histiocytic medullary reticulosis), and true histiocytic lymphoma are different presentations of Class III histiocytosis.

As used herein, therefore, the term "histiocytosis" is meant to encompass Classes I to III histiocytosis. Broadly, in that method, a mammalian host having histiocytosis is administered a composition containing a pharmacologically acceptable carrier having dissolved or dispersed therein, as an active ingredient, a 2-halo-2'-deoxyadenosine whose structure corresponds to that of previously discussed Formula I, or a pharmacologically acceptable acid addition salt thereof. The substituted adenine derivative, is present in the composition in an amount sufficient to provide a therapeutically effective dose over the period of administration.

The method of treatment presented herein is typically repeated periodically such as daily, weekly or monthly over a time period of one to several months to about one year. In the preferred pattern of administration, the active ingredient is administered daily for about 5 to about 7 days, followed two to four weeks later by another similar administration for a total of not more than two courses of administration. That series of courses of administration is then repeated at six months to yearly intervals, as required, for instance, if symptoms recur after a period of remission.

The amount of a compound of Formula I present in a composition and used in a method as described herein is a function of several variables, as is well known in the medicinal arts. The amount administered is less than that which substantially impairs bone marrow functions as determined by usual procedures.

The above amount of a 2-halo-2'-deoxyadenine derivative of Formula I or its pharmacologically acceptable salt present in the composition is also an amount sufficient to provide a therapeutically effective dosage ranging from about 0.5 to 0.9 mg/kg of body weight administered, preferably by infusion, over a course of from about 5 to 9 days, with the preferred course of administration being from about 0.05 to about 0.15 mg/kg/day, most preferably about 0.10 mg/kg/day for 5 to 7 days. Typically the dosage is administered in vivo, preferably by infusion, at about monthly intervals for no more than a total of two courses of treatment. It is most preferred that a single course of treatment be employed in treatment of Langerhans cell histiocytosis. This amount is another way of defining a therapeutically effective dose that is particularly useful when a compound of Formula 1 is administered by infusion.

The molar plasma concentration of the compound of Formula I or the pharmacologically acceptable salts thereof during treatment is preferably in the range of about 0.5 nanomolar (Nm) to about 100 nM, particularly about 1 nM to about 50 nM, and more preferably about 10 nM to about 20 nM. Molarity of the 2-halo-2'-deoxyadenine derivative in plasma of the treated (administered to) host animal thus provides still another measure of a therapeutically effective dose from which the amount in a composition can be calculated.

It is to be understood that the above therapeutically effective dosages need not be the result of a single administration, and are usually the result of the administration of a plurality of unit doses. Those unit doses can in turn comprise portions of a daily or weekly dosage, and thus, the therapeutically effective dose is determined over the period of treatment.

Unit dosage forms of the adenine derivative can contain about 0.1 milligrams to about 10 milligrams thereof. A preferred unit dosage form contains about 0.1 to about 1.5 milligram of agent and can be administered 1 to 5 times per day, or in combinations as desired to achieve the desired dosage. Administration can be orally, subcutaneously or by intraveneous injection, or by any other method known in the art. However, it should be noted that continuous infusion at a rate designed to maintain the above described plasma concentration is also contemplated.

As noted before, duration of a particular treatment can also vary, depending on severity of the disease. In the improved method of administration disclosed herein, the time course of administration is from about 5- to 7-days. Courses (cycles) of administration can also be repeated at monthly intervals, as disclosed herein or parenteral unit dosages can be delivered at weekly intervals.

Such an administration can be carried out on an outpatient basis for humans using an intravenous infusion lasting about 2 to about 4 hours in a doctor's office. As such, the treatment is far less invasive than is a continuous infusion over a period of several days that usually requires a hospital stay for the host mammal; i.e., human patient. A less invasive continuous infusion method that employs a pump linked to a catheter that automatically infuses a predetermined dosage permits the patient to be ambulatory during the infusion. A more preferred and still less invasive route of administration is by subcutaneous injection.

The efficacy of a method of this invention can be assessed in one or more of several reported procedures. One assay procedure is the histiocytosis Activity Index (CDAI) developed by the National Cooperative Histiocytosis Study Group and described in Best et al., *Gastroenterology*, 70:439–444 (1976). The CDAI provides a numerical score based upon eight mainly clinical variables those noted by the patient over a time period of one week.

The so-called "simple" index based on one day's entry of the CDAI values was shown by Harvey et al., *Lancet*, 1:514 (1980) to correlate well with the CDAI values and to be more easily used. That "simple" index is used here.

Another tool for measuring efficacy of a contemplated treatment method is whether the patient host mammal is able to lessen other medication taken to relieve the effects of his/her histiocytosis. There are two broad types of medications usually taken to treat histiocytosis: steroidal anti-inflammatory drugs such as prednisone, and other medications that can include additional anti-inflammatory medicaments such as azathioprine (Imuran) and anti-diarrheal medicaments such as lomotil. These drugs, although prescribed by a treating physician, are typically administered by the patients in their homes, and the amount of one or the other types of medication taken before and after administration of a contemplated method is ascertained by the patients themselves. Those amounts taken before and after a contemplated method are then compared. Such a comparison is another means by which efficacy is demonstrated here.

Disease state can also be assessed endoscopically using the histiocytosis Endoscopic Index of Severity (CDEIS) in types of histiocytosis in which clinical manifestations of the disease are found in the bowel. Endoscopic examinations are videotaped and then assessed by qualified gastroenterologists who are not aware of the treatment or lack thereof being given. Comparative radiologic studies of the small bowel before and after treatment are also useful in assessing efficacy.

Use of the "simple" CDAI and/or a lessening of anti-inflammatory or other histiocytosis-treating drugs can be used as the primary endpoints to demonstrate efficacy. Therapeutic outcomes are deemed successful if the "simple" CDAI is reduced by 50 percent or the use of one or the other histiocytosis-treating drugs is reduced by 50 percent at a time 12 weeks after beginning of a treatment method. The treatment regimen is typically stopped once one or more of the successful endpoints is reached.

A review of various methods for assessing severity and activity in histiocytosis is provided in Kjeldsen et al., *Scand. J. Gastroenterol.*, 28:1–9 (1993).

The following example illustrate the manner in which the invention can be practiced. It is understood, however, that the examples are for the purpose of illustration and the invention is not to be regarded as limited to any of the specific materials or conditions therein.

EXAMPLE 1

Three patients took part in a pilot study to assess the effect of an improved regimen for treatment of histiocytosis using 2-halo-2'-deoxyadenosine. Patient #1, the control patient, was treated using the prior art method of four courses of administration of the drug. Patient #'s 2 and 3 were administered the drug in accordance with the method of this invention wherein 2 courses (Patient #2) or 1 course of administration (Patient #3) was used. All Patients were required to have a histologic diagnosis of Langerhans-cell histiocytosis and measurable disease. The exemplary adenosine used, as 2-chloro-2'-deoxyadenosine (2-CdA)

(Ortho Biotech), was administered to each patient intravenously at 0.12 mg/kg/day for each of five consecutive days and the courses of administration were spaced at intervals of 28 to 35 days. Patients were tested for level of response and prohibitive toxicity after each course of administration. A complete response was defined as the absence of disease as proven by physical examination and imaging studies. Skin lesions did not require repeat biopsy to document histologic resolution. A partial response was defined as a reduction by more than 50% of all measurable disease for more than one month. Any response less than partial was designated as no response. Standard criteria of the Eastern Cooperative Oncology Group were used for the evaluation of toxicity as described in M. M. Oken et al., *Am. J. Clin. Oncol.* 5:649–655, 1982, which is incorporated herein by reference.

Each of the three patients had refractory histiocytosis and was taking prednisone as well as another medication at the time the study began. The patients were permitted to continue their prior therapies as needed during this study, and they monitored the amounts of supplementary medication taken, particularly any lessening in those amounts. One patient had pre- and post-treatment endoscopies.

Patient #1, the control patient, was a 33-year old woman who presented at age 15 years with polyuria and polydipsia from diabetes insipidus and later developed vesiculopustular lesions of her gingiva, scalp, and vagina. At the time of treatment Patient #1 had numerous 3- to 4 mm vesiculopustular lesions and shallow ulcers of her scalp, buccal mucosa, vagina, and external auditory canals. She was assessed as having stage II histiocytosis as scored according to Lavin and Osband, *Hematol. Oncol. Clin. North Am.,* 1:35–47, 1982.

During each course of 2-CdA, blood monocytes completely disappeared. The median absolute monocyte count before treatment was $0.28 \times 10^9$/L (range 0.09 to $0.38 \times 10^9$/L); after 48 hours of 2-CdA treatment, the count was $0.09 \times 10^9$/L (range 0.05 to $0.38 \times 10^9$/L. On day 7, the count was $0.0 \times 10^9$/L during all four courses. A peripheral blood immunophenotypic analysis done after the second 2-CdA course showed a CD4 cell count of 137 cells/mL and a CD8 cell count of 76 cells/mL (CD4/CD8 ratio, 1.61 ). After three courses of 2-CdA, the CD4 cell count was 175 cells/mL and the CD8 cell count was 464 cells/mL (CD4/CD8 ratio, 0.38). Six months after the fourth course of 2-CdA, the CD4 count was 202 cells/mL, and the CD8 cell count was 307 cells/mL (CD4/CD8 ratio, 0.66).

Patient #2 was a 57-year-old man with a two year history of erythematous patches and scattered papular lesions involving his scalp, external auditory canals, axillae, and scrotal areas with associated lymphadenopathy or hepatosplenomegaly. Biopsy specimens of these skin lesions confirmed Langerhans-cell histiocytosis and showed positive for the S-100 protein immunohistochemical stain. Intracytoplasmic Birbeck granules were identified on electron microscopy. Before treatment, the leukocyte count was $3.1 \times 10^9$/L, the absolute neutrophil count was $1.3 \times 10^9$, the hemoglobin concentration was 146 g/L, and the platelet count was $147 \times 10^9$. The bone marrow, chest radiograph, bone scan, bone survey, and CT scan of the abdomen were all normal. Because of neutropenia, Patient #2 was ranked at Stage III according to Lavin and Osband criteria. Two courses of 2-CdA at 0.7 mg/kg per course given over 7 days by continuous infusion were administered. The second course was delayed beyond the 28–35 spacing interval because of protracted grade 3 neutropenia and mild thrombocytopenia. Three months after the last course of 2-CdA, all lesions resolved and the patient remained in complete remission for more than 15 months. On follow up, the leukocyte count was $2.6 \times 10^9$/L, the absolute neutrophil count was $0.8 \times 10^9$/L, the hemoglobin concentration was 134 g/L, and the platelet count was $100 \times 10^9$/L.

Patient #3 was a 51-year-old woman with a 10-year history of cutaneous involvement by Langerhans cell histiocytosis. She had extensive nonpruritic erythematous papular lesions involving her face, chest, extremities, and perineum. She had been treated with vinblastine with partial response, and psoralen plus UV-A exposure without benefit. Due to absence of organ dysfunction, this patient was ranked at Stage II according to Lavin and Osband criteria. Patient #3 was treated with 2-CdA at 0.7 mg/kg of body weight (0.14 mg/kg/day) in a single course of treatment given over 5 days by 2-hour intravenous infusions. She developed transient grade 3 neutropenia within one week of completing the course of 2-CdA therapy that fully resolved by week two. Surprisingly, one month after her first course of 2-CdA, her symptoms and skin lesions improved, and a complete clinical remission was achieved at two months. She received a second course of 2-CdA without complications, and her skin biopsy-confirmed complete remission had continued for more than five months at the time of the report.

As can be seen from the comparative data in Table 1, below, whose data represent results at three months (12 weeks) after the start of therapy, all three patients exhibited significant improvement of all clinically relevant endpoints. No significant side effects were observed. The patient who had pre- and post-treatment endoscopies showed complete resolution of mucosal ulceration and inflammation. In addition, at six months after starting therapy, patient #3 no longer required prednisone and was no longer taking any medication to treat the disease.

TABLE 1

|  | Before Treatment | After Treatment | Percent Reduction |
|---|---|---|---|
| Prednisone (mg) (mg/day) | | | |
| Patient #1 (control) | 30 | 0 | 100 |
| Patient #2 | 10 | 5.5 | 50 |
| Patient #3 | 20 | 5 | 75 |
| CDAI (Simple Index) | | | |
| Patient #1 (control) | 8 | 3 | 63 |
| Patient #2 | 18 | 16 | 11 |
| Patient #3 | 11 | 6 | 45 |
| Other Medications (mg/day) | | | |
| Patient #1 (control) | 5–20* | 0 | 100 |
| Patient #2 | 2400** | 0 | 100 |
| Patient #3 | 100*** | 0 | 100 |

*Lomotil
**Asacol
***Azathioprine

The foregoing description is intended as illustrative and is not to be taken as limiting. Still other variations within the spirit and scope of this invention are possible and will readily present themselves to those skilled in the art.

We claim:

1. A method for treating Class I histiocytosis in a mammal in need thereof comprising administering to said mammal a therapeutically effective dose of a substituted adenine derivative or a pharmacologically acceptable acid addition salt thereof, in an amount of about 0.5 to 0.9 mg/kg of body weight over a course of about 5 to 9 days, said adenine derivative having a structure represented by the formula:

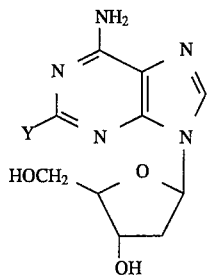

wherein Y is a halogen, and wherein no more than two courses of treatment are administered.

2. The method of claim 1, wherein the courses are spaced by an interval of from 28 to 35 days.

3. The method of claim 1 wherein said adenine derivative is administered in an amount of about 0.1 mg/kg of body weight per day over a course of about 5 to 7 days.

4. The method of claim 1 wherein the halogen is a chlorine.

5. The method of claim 1 wherein said mammal is a human.

6. The method of claim 1 wherein the administering is by continuous infusion.

7. The method of claim 6 wherein the halogen is a chlorine.

8. A method for treating Class I histiocytosis in a human patient comprising administering to said patient a substituted adenine derivative or a pharmacologically acceptable acid addition salt thereof in an amount of about 0.05 to about 0.15 milligrams per kilogram of body weight per day over a course of about 5 to 9 days dissolved or dispersed in a pharmacologically acceptable carrier, said adenine derivative having a structure represented by the formula:

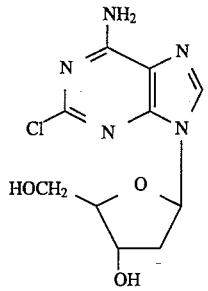

wherein no more than two courses are administered.

9. The method of claim 8, wherein said adenine derivative is administered in an amount of about 0.1 mg/kg of body weight per day over a course of about 5 to 7 days.

10. The method of claim 8 wherein the courses of treatment are spaced at an interval of about 28 to 35 days, 11. The method of claim 8 wherein the administering is by continuous infusion.

12. The method of claim 8 wherein the administering is by continuous infusion.

* * * * *